(12) United States Patent
Gogolewski

(10) Patent No.: US 6,461,632 B1
(45) Date of Patent: Oct. 8, 2002

(54) HARDENABLE CERAMIC HYDRAULIC CEMENT

(75) Inventor: Sylwester Gogolewski, Davos (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/836,267

(22) Filed: Apr. 18, 2001

Related U.S. Application Data

(63) Continuation of application No. PCT/EP98/06595, filed on Oct. 19, 1998.

(51) Int. Cl.⁷ .............................. A61F 2/28; A61F 2/30; A61F 2/00
(52) U.S. Cl. ........................ 424/426; 424/423; 424/422; 514/772.3
(58) Field of Search ........................... 623/16.11, 23.61, 623/23.72, 23.62; 424/423, 426, 422; 514/772.3

(56) References Cited

U.S. PATENT DOCUMENTS

| | | | |
|---|---|---|---|
| 4,596,574 A | 6/1986 | Urist | 623/16 |
| 5,082,808 A * | 1/1992 | Nonami et al. | 501/95 |
| 5,149,368 A * | 9/1992 | Liu et al. | 424/602 |
| 5,336,264 A * | 8/1994 | Constanz et al. | 623/16 |
| 5,648,097 A * | 7/1997 | Nuwayser | 424/489 |
| 6,214,048 B1 * | 4/2001 | Ito et al. | 623/16.11 |

FOREIGN PATENT DOCUMENTS

| | | |
|---|---|---|
| JP | 03109077 A * | 5/1991 |
| WO | WO 98/08773 | 3/1998 |
| WO | WO 99/17710 | 4/1999 |

* cited by examiner

*Primary Examiner*—Thurman K. Page
*Assistant Examiner*—Rachel M. Bennett
(74) *Attorney, Agent, or Firm*—Pennie & Edmonds LLP

(57) ABSTRACT

A method for delivering a therapeutically effective drug via a hardenable ceramic hydraulic cement composition including a first component of at least one sodium or calcium salts of inorganic and organic acids, a second component of at least one alkaline, and optionally third and fourth components including an organic carboxylic acid and pure water, respectively, wherein the cement composition is implanted in an animal or human body, hardens, and then degrades in situ after time to releases a amount of the drug into a locally targeted area.

34 Claims, No Drawings

HARDENABLE CERAMIC HYDRAULIC CEMENT

CROSS-REFERENCE TO RELATED APPLICATION

This application is a continuation of International Application No. PCT/EP98/06595, filed Oct. 19, 1998, the disclosure of which is hereby incorporated herein by express reference thereto.

FIELD OF INVENTION

This invention is directed to a method for delivering a drug via a hardenable ceramic hydraulic cement composition, implanted in an animal or human, that both hardens and dissolves or degrades in situ after time to release a therapeutically effective amount of the drug into a locally targeted area. The invention further relates to the cement composition obtainable according to the method described, including a first component of at least one sodium or calcium salt of inorganic and organic acids, a second component of at least one alkaline, and optionally third and fourth components including an organic carboxylic acid and pure water, respectively.

BACKGROUND OF THE INVENTION

Ceramic cements which harden in situ can be used for various applications. Such cements may be applied to reinforce porotic bones, to enhance fixation of fractures of porotic bones, to fill bone defects or to release bone growth factors.

Recently, resorbable cements, consisting of β-tricalciumphosphate, monocalcium phosphate and so-called carbonized cements containing calcium carbonate, became known that set at body temperature. These known cements have the disadvantage of long resorption or dissolution times. While this property is indispensable when cements are used to enhance bone fracture fixation, it is undesirable when cements are applied as carriers for fast local delivery of drugs.

The invention as claimed aims at solving both of the above described problems.

SUMMARY OF THE INVENTION

The invention relates to a ceramic hydraulic cement composition that includes a first component including at least one of a calcium or sodium salt of an inorganic and/or organic acid and a second component including an alkaline component. The invention also related to a method of delivering the composition which includes providing a first component including at least one of a calcium or sodium salt of an inorganic and/or organic acid; providing a second component including an alkaline component; mixing the first and second components to form a ceramic hydraulic cement composition; and implanting a therapeutically effective amount of the composition into an animal or human, preferably human. The composition hardens in situ and degrades in situ after a period of time to release a drug to a locally targeted area, preferably a bone defect. The composition preferably degrades within 10 hours to 4 months, preferably within 10 hours to 30 days.

The calcium or sodium salt can include carbonic acid, phosphoric acid, or glycerophosphoric acid, or mixtures thereof. Preferably, wherein the salt includes at least one of hydroxyapatite, tricalcium phosphate, calcium carbonate, calcium hydrogen phosphate, disodium hydrogen phosphate, or calcium glycerophosphate. The first component can further include a therapeutically active agent.

The second component preferably includes sodium silicate or calcium silicate and is preferably present in the composition in an amount from 0.01 to 10 weight percent. In one embodiment, the second component also includes water.

In another embodiment, the composition further includes a third component, preferably an organic carboxylic acid, and more preferably at least one of ascorbic acid, citric acid, or tartaric acid.

In one embodiment, the composition includes an osteogenic agent., preferably at least one of growth factors, osteocalcines, calcium binding proteins, bone morphogenetic proteins, antimicrobial agents, or vitamins.

DETAILED DESCRIPTION OF THE PREFERRED EMBODIMENTS

The present invention provides a method for delivering a composition by implanting a hardenable ceramic hydraulic cement into a body, as defined in the claims. The main advantage of the invention is the relatively short dissolving time of the hardened implanted cement compared to the above mentioned prior art cements which allows for faster delivery of drugs, in particular of osteogenic drugs.

In a preferred embodiment of the invention, a further component C, which is an organic carboxylic acid, is used. The organic carboxylic acid may be chosen from the group of ascorbic acid, citric acid or tartaric acid and has the function of neutralizing the alkaline components (sodium or calcium silicate) of the cement. Further advantages are the better compatibility with the environment and the faculty to complex calcium ions from the body fluids more easily and to deposit in the bone defect treated with the cement. The use of ascorbic acid, in particular, further contributes to the formation of collagen in the bone defect treated with the cement.

Component A may preferably comprise calcium and/or sodium salts of carbonic acid, phosphoric acid or glycerophosphoric acid which are highly biocompatible, in particular if selected from the group of hydroxyapatite (HA), tricalcium phosphate (TCP), calcium carbonate, calcium hydrogen phosphate, disodium hydrogen phosphate or calcium glycerophosphate.

In a preferred embodiment water is incorporated in component B prior to mixing in order to obtain a shorter mixing time.

In a more preferred embodiment, the concentration of the aqueous solution of sodium or calcium silicate of component B is in the range of 0.01% to 10.00% which facilitates preparation of the cement and thus contributes in controlling the acidity thereof.

In a further preferred embodiment, the drugs added to the cement are chosen from the group of: osteogenic drugs, tissue growth factors (TGF-beta), osteocalcines, calcium binding proteins (GLA), bone morphogenetic proteins (BMP), antimicrobial drugs or vitamins. The concentration is specific for the particular application and drug used.

EXAMPLES

The various features of novelty which characterize the invention are pointed out with particularity in the claims appended to and forming part of this disclosure. For better understanding of the invention, its operating advantages and specific objects attained by its use, the following nonlimiting examples, which are merely illustrative of the preferred embodiments of the present invention, and are not to be construed as limiting the invention, are incorporated as reference.

Example 1

5 parts by weight of calcium glycerophosphate and 1.5 parts by weight of 0.001-% aqueous solution of sodium silicate were mixed together and place in a plastic cylindrical mold. The mixture set within 60 to 90 minutes, and disintegrated when placed in water within 7 hours.

Example 2

3 parts by weight of hydroxyapatite (HA) and 1 part by weight of ascorbic acid were mixed with 2 parts by weight of water and 0.1 parts by weight of sodium silicate. The mixture set within 10 to 20 minutes, and disintegrated when placed in water within 40 hours.

Example 3

3 parts by weight of tricalcium phosphate (TCP) and 1 part by weight of ascorbic acid were mixed with 2 parts by weight of water and 0.1 parts by weight of sodium silicate. The mixture set within 10 to 20 minutes, and disintegrated when placed in water within 30 hours.

Example 4

3 parts by weight of hydroxyapatite (HA) and 1 part by weight of ascorbic acid were mixed with 1 part by weight of water and 0.1 part by weight of calcium silicate. The mixture set within 15 minutes, and disintegrated when placed in water within 50 hours.

Example 5

3 parts by weight of tricalcium phosphate (TCP) and 1 part by weight of ascorbic acid were mixed with 1 part by weight of water and 0.1 part by weight of calcium silicate. The mixture set within 15 minutes, and disintegrated when placed in water within 12 hours.

Example 6

2 parts by weight of hydroxyapatite (HA) were mixed with I part by weight of an aqueous solution sodium silicate (glass water) and 0.2 part by weight of ascorbic acid. The paste was mixed for 5 minutes and the paste obtained was allowed to set for 5 hours. When placed in water or saline solution it dissolved within 12 hours.

Example 7

2 parts by weight of tricalcium phosphate (TCP) were mixed with 1 part by weight of an aqueous solution of sodium silicate (glass water) and 0.2 part by weight of ascorbic acid. The paste was mixed for 5 minutes and the paste obtained was allowed to set for 5 hours. When placed in water or saline solution it dissolved within 12 hours.

Example 8

2 parts by weight of hydroxyapatite (HA) were mixed with 1 part by weight of ascorbic acid and 0.1 part by weight of an aqueous solution of sodium silicate (glass water). The paste obtained set within 15 minutes and dissolved when placed in water within 40 days. Increasing the amount of ascorbic acid in the cement mixture decreases time required for the cement setting and extends the dissolution time in water.

Example 9

2 parts by weight of tricalcium phosphate (TCP) were mixed with 0.5 parts by weight of ascorbic acid and 0.1 part by weight of an aqueous solution of sodium silicate (glass water). The paste obtained set within 15 minutes and dissolved when placed in water within 40 days. Increasing the amount of ascorbic acid in the cement mixture decreases time required for the cement setting and extends the dissolution time in water.

Example 10

2 parts by weight of calcium carbonate were mixed with 1 part by weight of an aqueous solution of sodium silicate (glass water) and 1 part by weight of ascorbic acid. The cement set within 20 minutes and dissolved in water within 40 days.

Example 11

2 parts by weight of calcium carbonate were mixed with 1 part by weight of an aqueous solution of sodium silicate (glass water) and 0.5 parts by weight of ascorbic acid. The cement set within 20 minutes and dissolved in water within 30 days.

Example 12

3 parts by weight of tricalcium phosphate (TCP) were mixed with 3 parts by weight of calcium glycerol phosphate and 0.5 parts of ascorbic acid, 0.01 parts by weight of an aqueous solution of sodium silicate (glass water) and 1 part of water. The paste obtained set within 30 minutes. Disintegration time in water was from 10 days.

Example 13

4 parts by weight of calcium glycerophosphate, 0.01 part by weight of an aqueous solution of sodium silicate (glass water) and 0.05 part by weight 1 wt-% aqueous solution of ascorbic acid were mixed together with 1 part by weight of deionised water. The resulting paste set within 1 hour the paste disintegration.

Example 14

In this example the cement composition is stored in three separate containers X, Y and Z. Container X contained 10 parts by weight of calcium carbonate. Container Y contained 2 parts by weight of ascorbic acid. Container Z contained sodium silicate dissolved in water (glass water of the density in the range of 1.3 to 1.4 g/ml. For initiating the hardening process the liquid in container Z was put into contact with the powder of container X and subsequently the liquid in container Y was added. The resulting paste was mixed either by hand with a spatula or mechanically in mixing bowl.

Physical Properties of the Hardened Cements According to the Examples

The hardened cements showed a tensile strength in the range of 0.6 to 5.0 MPa; most of them in the range of 1 to 3 MPa.

Depending on the chemical composition, the hardened cement mixtures according to the invention dissolve when placed in water within 10 hours to 4 months. The short dissolution times from 10 hours to 30 days are preferably when cements are used for local delivery of osteogenic drugs (e.g., growth factors).

Salts used for preparation of cements should be of non-toxic nature. Acidity (pH-value) of the cements can be adjusted by changing the composition.

Glass water contains either sodium compounds in a form as expressed in $Na_2O$ between 6 to 1% or silica compounds as expressed in $SiO_2$ from 10 to 50%.

While the foregoing description and drawings represent the preferred embodiments of the present invention, it will be obvious for those of ordinary skill in the art that various changes and modifications may be made therein without departing from the true spirit and scope of the present invention.

What is claimed is:

1. A method of delivering a composition which comprises:
   providing a first component comprising at least one of a calcium or sodium salt of an inorganic and/or organic acid;
   providing a second component comprising sodium silicate or calcium silicate;
   mixing the first and second components to form a ceramic hydraulic cement composition; and
   implanting a therapeutically effective amount of the composition into an animal,
   wherein the first component is different from the second component,
   wherein the composition hardens in situ,
   and wherein the composition degrades in situ over a period of time to release a drug to a locally targeted area.

2. The method of claim 1, wherein the inorganic and/or organic acid comprises carbonic acid, phosphoric acid, or glycerophosphoric acid.

3. The method of claim 2, wherein the calcium or sodium salt comprises at least one of hydroxyapatite, tricalcium phosphate, calcium carbonate, calcium hydrogen phosphate, disodium hydrogen phosphate, or calcium glycerophosphate.

4. The method of claim 1, wherein the first component further comprises a therapeutically active agent and the animal is human.

5. The method of claim 1, wherein the second component comprises an aqueous solution of sodium silicate or calcium silicate.

6. The method of claim 1, wherein the second component further comprises water.

7. The method of claim 6, wherein the amount of the sodium silicate or calcium silicate in the second component is from 0.01 to 10 weight percent.

8. The method of claim 1, wherein the composition further comprises a third component comprising an organic carboxylic acid.

9. The method of claim 8, wherein the third component comprises at east one of ascorbic acid, citric acid, or tartaric acid.

10. The method of claim 8, wherein the third component comprises ascorbic acid.

11. The method of claim 1, wherein the composition degrades in 10 hours to 4 months.

12. The method of claim 11, wherein the composition degrades in 10 hours to 30 days.

13. The method of claim 1, wherein the locally targeted area is a bone defect.

14. The method of claim 1, wherein the composition further comprises an osteogenic agent.

15. The method of claim 14, wherein the osteogenic agent comprises at least one of growth factors, osteocalcines, calcium binding proteins, bone morphogenetic proteins, antimicrobial agents, or vitamins.

16. A ceramic hydraulic cement composition comprising:
   a first component comprising at least one of a calcium or sodium salt of an inorganic and/or organic acid;
   a second component comprising sodium silicate or calcium silicate; and
   a third component comprising an organic carboxylic acid,
   wherein the first component is different from the second component, and
   wherein the composition degrades in the presence of water in 10 hours to 4 months.

17. The composition of claim 16, wherein the inorganic and/or organic acid comprises carbonic acid, phosphoric acid, or glycerophosphoric acid.

18. The composition of claim 17, wherein the calcium or sodium salt comprises at least one of hydroxyapatite, tricalcium phosphate, calcium carbonate, calcium hydrogen phosphate, disodium hydrogen phosphate, or calcium glycerophosphate.

19. The composition of claim 16, wherein the first component comprises therapeutically active agent and the animal is human.

20. The composition of claim 16, wherein the composition further comprises at least one of growth factors, osteocalcines, calcium binding proteins, bone morphogenetic proteins, antimicrobial agents, or vitamins.

21. The composition of claim 16, wherein the composition degrades in water in 10 hours to 30 days.

22. The composition of claim 16, wherein the second component comprises an aqueous solution of sodium silicate or calcium silicate.

23. The composition of claim 16, wherein the second component further comprises water.

24. The composition of claim 23, wherein the amount of the sodium silicate or calcium silicate in the second component is from 0.01 to 10 weight percent.

25. The composition of claim 16, wherein the composition further comprises a fourth component comprising pure water.

26. The composition of claim 25, wherein the third component comprises at least one of ascorbic acid, citric acid, or tartaric acid.

27. A method of delivering a composition which comprises:
   providing a first component comprising at least one of a calcium or sodium salt of an inorganic and/or organic acid;
   providing a second component comprising sodium silicate or calcium silicate;
   providing a third component comprising an organic carboxylic acid;
   mixing the first, second, and third components to form a ceramic hydraulic cement composition; and
   implanting a therapeutically effective amount of the composition into an human, wherein the first the component is different from the second component,
   wherein the composition hardens in situ,
   and wherein the composition degrades in situ over a period of time to release a drug to a locally targeted area.

28. The method of claim 27, wherein the inorganic and/or organic acid comprises carbonic acid, phosphoric acid, or glycerophosphoric acid.

29. The method of claim 28, wherein the calcium or sodium salt comprises at least one of hydroxyapatite, tricalcium phosphate, calcium carbonate, calcium hydrogen phosphate, disodium hydrogen phosphate, or calcium glycerophosphate.

30. The method of claim 8, wherein the first component further comprises a therapeutically active agent and the animal is human.

31. The method of claim 8, wherein the second component further comprises water, and wherein the amount of the sodium silicate or calcium silicate in the second component is from 0.01 to 10 weight percent.

32. The method of claim 8, wherein the third component comprises at least one of ascorbic acid, citric acid, or tartaric acid.

33. The method of claim 8, wherein the composition degrades in 10 hours to 4 months.

34. The method of claim 30, wherein the locally targeted area is a bone defect and wherein the therapeutically active agent comprises at least one osteogenic agent comprising growth factors, osteocalcines, calcium binding proteins, bone morphogenetic proteins, antimicrobial agents, or vitamins.

* * * * *